United States Patent
Grasset et al.

(10) Patent No.: US 7,763,600 B2
(45) Date of Patent: Jul. 27, 2010

(54) HORMONE-BASED NITROGEN MONOXIDE DONOR COMPOUNDS AND USE THEREOF IN OBSTETRICS AND GYNECOLOGY

(75) Inventors: Etienne Robert Alfred Grasset, Boulogne-Billancout (FR); Felix Mendez, Madrid (ES); Carlo Pavan, Nogent sur Marne (FR); Didier Terracol, Vernieres le Buisson (FR)

(73) Assignee: EFFIK, Bievres (FR)

( * ) Notice: Subject to any disclaimer, the term of this patent is extended or adjusted under 35 U.S.C. 154(b) by 1386 days.

(21) Appl. No.: 10/520,637

(22) PCT Filed: Jul. 9, 2003

(86) PCT No.: PCT/FR03/02152
§ 371 (c)(1),
(2), (4) Date: Jan. 7, 2005

(87) PCT Pub. No.: WO2004/007522
PCT Pub. Date: Jan. 22, 2004

(65) Prior Publication Data
US 2005/0222105 A1    Oct. 6, 2005

(30) Foreign Application Priority Data
Jul. 9, 2002    (FR) .................................. 02 08619

(51) Int. Cl.
*A61K 31/57*    (2006.01)
*C07J 5/00*    (2006.01)

(52) U.S. Cl. ...................................... 514/182; 552/600
(58) Field of Classification Search ................. 552/600; 514/182
See application file for complete search history.

(56) References Cited

U.S. PATENT DOCUMENTS

| 3,052,675 A | 9/1962 | Berlin et al. |
| 3,352,891 A | 11/1967 | Wendt et al. |
| 3,494,941 A | 2/1970 | Ledig et al. |

FOREIGN PATENT DOCUMENTS

| GB | 1 446 126 | 8/1976 |
| WO | WO 98/09948 | 3/1998 |
| WO | WO 2004/007522 A3 | 1/2004 |

OTHER PUBLICATIONS

Hodosan et al., "Nitrate esters of seroid hormones and related compounds. Preparation and biological properties." Arzneimittel-Forschung, vol. 19(4), pp. 684-685, 1969.*

* cited by examiner

*Primary Examiner*—Barbara P Badio
(74) *Attorney, Agent, or Firm*—Charles Muserlian

(57) ABSTRACT

The invention concerns compounds capable of being fixed on hormone receptors and having a nitrogen monoxide donor group and their use for preventing premature births, increasing cervical dilatation, for use in hormone substitution therapy as anti-hypertensive drug and their therapeutic use for preparing a medicine for use in obstetrics and gynecology.

8 Claims, No Drawings

HORMONE-BASED NITROGEN MONOXIDE DONOR COMPOUNDS AND USE THEREOF IN OBSTETRICS AND GYNECOLOGY

This application is a 371 of PCT/FR2003/002152 filed Jul. 9, 2003.

The present invention relates to compounds capable of binding to hormone receptors and having a nitrogen monoxide-donor nitric ester group, to the use thereof for preventing premature births and increasing cervical dilatation during labor, in the context of hormone replacement therapy or as antihypertensive, and to the therapeutic use thereof for preparing a medicinal product for use in obstetrics and gynecology.

Premature births remain relatively common, representing from 5 to 10% of all pregnancies. This proportion has not changed in the last 20-30 years.

An adequate secretion of progesterone is in fact necessary in order to maintain the pregnancy to term. Progesterone is a hormone that is initially secreted by the corpus luteum, or yellow body, in the ovary and then by the placenta. Inhibition of uterine contractility by progesterone or progesterone derivatives has been demonstrated using pharmacological animal models.

The administration of progesterone during the third trimester of pregnancy, in order to prevent delivery before maturity of the child, was already evoked more than 20 years ago. As a result of this, micronized progesterone was administered very commonly in France, at high oral doses (most commonly at least 600 mg per day), to women in order to prevent a premature birth. This use was, however, stopped subsequent to a risk of liver toxicity related to the treatment. In addition, this treatment did not in fact have any really proved effect on the birth weight and the gestation age of children.

It has very recently been shown that a treatment by weekly injection of a progesterone derivative makes it possible, in women at very high risk, to reduce the frequency of premature births and to decrease the frequency of certain complications in their children [Meis P J, Klebanoff M, Thom E et al. *Prevention of recurrent preterm delivery by 17 alpha-hydroxyprogesterone caproate. N Engl J Med* 2003; 348:2379-85].

Nitrogen monoxide has recently been identified as being an important modulator of cell function. It has a potent relaxing effect-on smooth muscle cells. In fact, glyceryl trinitrate had been used for many years to treat symptoms of angina well before its mechanism of action was known (glyceryl trinitrate is a nitrogen monoxide donor).

The uterine muscle, the myometrium, also contains-smooth muscle cells. Nitrogen monoxide synthase, the enzyme which synthesizes nitrogen monoxide, thus has a relaxing effect on the muscle cells of the uterine myometrium and of the cervix. Nitrogen monoxide also increases uterine blood flow during pregnancy.

In vivo, inhibiting the production of nitrogen monoxide causes premature parturition in gestating guinea pigs. Conversely, local application of sodium nitroprusside, which is a nitrogen monoxide donor, to the cervix, at term, increases cervical dilatation. This shows that nitrogen monoxide may have two different effects, on the body of the uterus, and on the cervix. Inhibiting uterine contraction relaxes the body of the uterus and can prevent a premature birth, preterm. When the term is reached, the induction of a softening and of a dilatation of the cervix may aid in the progression of the birth.

Nitric acid donor groups, such as glyceryl trinitrate, have thus been evaluated in women in order to test the induction of uterine relaxation. Patients whose condition required urgent tocolysis for placental retention, for problems of difficult fetal extraction or for acute uterine inversion were treated with an initial intravenous dose of 50 to 500 micrograms of nitroglycerine with repeated boluses 60 to 90 seconds apart.

Despite the effectiveness of this treatment, the occurrence of transient hypotension was noted in 41% of cases, despite intravenous hydration [O'Grady J P, Parker R K, Patel S S, *Nitroglycerin for rapid tocolysis: development of a protocol and a literature review. J. Perinatology* 2000; 1:27-33].

The administration of nitroglycerine by means of a transdermal patch capable of delivering 0.4 mg/hour of nitroglycerine was tested on a total of 33 women presenting preterm labor, and compared with a placebo. These women received a prophylactic intravenous administration of 1000 ml of a 0.9% saline solution for 1 to 2 hours in order to prevent the nitroglycerine-induced hypotension. There were fewer births within 48 hours among the women who received the nitroglycerine. However, the sample size was too small for it to be statistically interpretable.

A larger study compared the effectiveness of transdermal glyceryl trinitrate by means of patches of 10 or 20 mg, to an intravenous injection of ritodrine, in order to avoid a preterm delivery. The results obtained show that the effectiveness of these two treatments is similar [Lees C C, Lojacono A, Thompson C, Danti L, Black R S, Tanzi P et al. *Glyceryl trinitrate and ritodrine in tocolysis: an international multicenter randomized study. Obstet Gynecol* 1999; 94:403-8]. The most common adverse effect observed with ritodrine was tachycardia; for glyceryl trinitrate, it was headaches.

Patent WO 95/13802 describes the use of a substrate of nitrogen monoxide synthase and/or of a nitrogen monoxide donor with various compounds, including a progestogen, in order to inhibit uterine contraction, or a nitrogen monoxide inhibitor with a progesterone antagonist in order to stimulate uterine contractility.

U.S. Pat. No. 5,895,783 describes the simultaneous administration of three compounds, a progestogen, a nitric oxide synthase substrate or a nitric oxide donor and various compounds for anti-inflammatory purposes, such as cyclooxygenase inhibitors, in women exhibiting eclampsia with or without preterm labor.

Nitroglycerine, arginine and progesterone are administered in separate compositions. However, the progesterone dose must be very high in order to be equivalent to an amount of 50 to 300 mg of injected progesterone.

U.S. Pat. No. 5,595,970 describes the use of a nitrogen monoxide substrate and/or of a nitric oxide donor alone or in combination with a progestogen, an estrogen or both in order to reduce the occurrence of symptoms related to the menopause. In this case, the amount of progestogen is equivalent to a dose of 50 to 300 mg of injected progesterone, which is extremely high.

U.S. Pat. No. 6,040,340 describes a method for improving the pregnancy rate by administration of a nitrogen monoxide substrate and/or of a nitric oxide donor alone or in combination with a progestogen and, optionally, with an estrogen, or a contraceptive method. Here again, a very high dose of progestogen was used.

U.S. Pat. No. 6,028,106 describes a similar method for relaxing the bladder detrusor muscle and treating urinary incontinence.

Patent WO 98/09948 describes the use of nitric oxide-derived compounds which can relax smooth muscle and help to control urinary incontinence and other pathologies, which include preterm delivery. A combination of a group capable of releasing nitrogen monoxide with corticosteroids was considered only with the aim of increasing the anti-inflammatory properties of these corticoids.

The Applicant has discovered a family of compounds capable of binding to hormone receptors and comprising a nitrogen monoxide-donor nitric ester group, with the exception of estradiol substituted in the 11- and/or 17-position with a nitric ester group. It has discovered that these compounds exert a therapeutic action in the prevention of premature births, in the control of uterine mobility, in increasing cervical dilatation during labor, in anomalies of uterine contraction, in dysmenorrhea, in hormone replacement therapy in menopausal women, in the induction of an endometrial cycle in the context of assisted reproduction, and in the prevention of hypertension.

A subject of the invention is therefore compounds capable of binding to hormone receptors and comprising a nitrogen monoxide-donor nitric ester group, with the exception of estradiol substituted in the 11- and/or 17-position with a nitric ester group.

The hormone receptors are chosen from steroid receptors, retinoid receptors and vitamin D derivative receptors.

The preferred compounds according to the invention, capable of binding to hormone receptors, may be natural or synthetic hormones that act as an agonist or antagonist after binding to the appropriate hormone receptor, comprising one or more nitric ester groups. The compounds according to the invention bind to hormone receptor-rich tissues. The presence of these groups in these molecules offers several advantages:

modifications of physicochemical properties of these molecules with, for example, an improvement in water-solubility of the least polar molecules, modification of the metabolism of these molecules, possibility of delivery of nitrogen monoxide in the tissues.

These hormones are preferably progestogens, estrogens, antimineralocorticoids, androgens, antiandrogens or a combination of these hormones.

These hormones are chosen more particularly from progesterone, 17OH-progesterone, estradiol, ethinyl estradiol, aldosterone, spironolactone, drospirenone, testosterone and cyproterone.

These hormones comprise at least one or more NO-donor nitric ester groups.

Preferably, the compound comprises one or more $NO_2$ groups bonded to the hormone directly via the oxygen atom of the enolic form or by means of a benzyloxy radical.

Preferably, the hormone capable of binding to hormone receptors is progesterone or 17OH-progesterone comprising one or more $NO_2$ groups bound directly or by means of a benzyloxy radical.

In particular, when the $NO_2$ group(s) is (are) bonded directly to the hormone, the bonding occurs via the oxygen atom of the enolic form of the hormone, for example in the 3-position of progesterone or in the 17-position of 17OH-progesterone.

When the $NO_2$ group(s) is (are) bonded to the hormone by means of a benzyloxy radical, this bonding occurs either directly to the hormone, or by means of a group that establishes a bridge, such as a C=O or COO group, with the oxygen atom of the enolic form of the hormone or directly on the ring such as, for example, in the 3-position of progesterone or in the 3- and/or 17-position of 17OH-progesterone.

The compounds according to the invention may comprise $NO_2$ groups bonded in one of the positions directly to the hormone and, in the other position, bonded by means of a benzyloxy group.

These hormones may have the formula below:

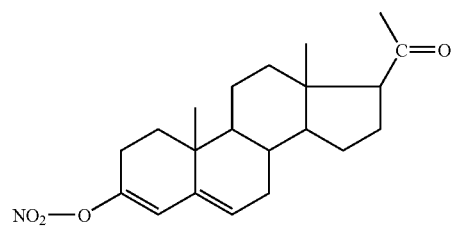

(I)

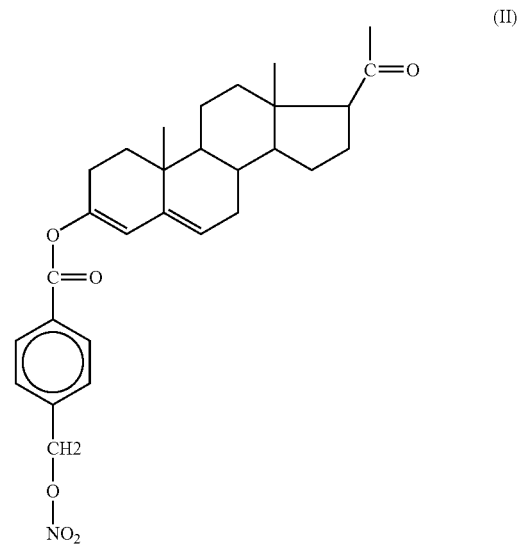

(II)

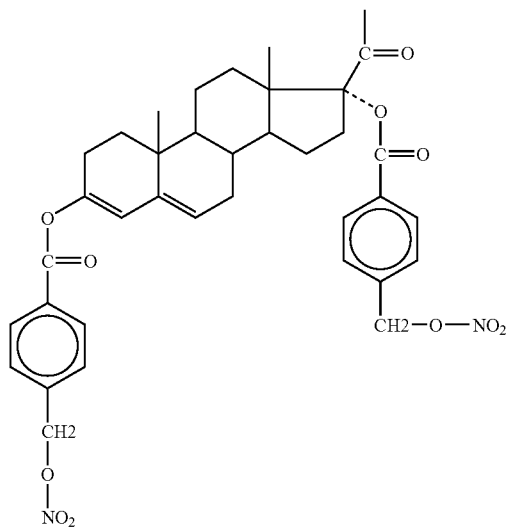

(III)

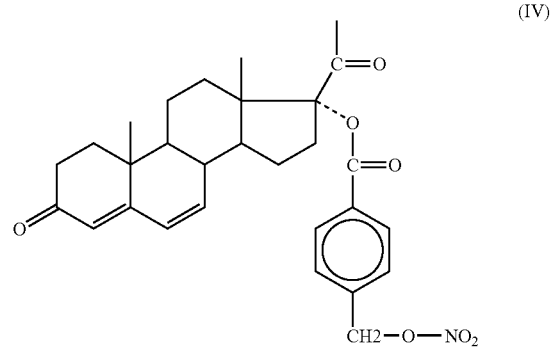

(IV)

In another embodiment of the invention, the hormone capable of binding to hormone receptors is estradiol comprising, in the 17- and in the 3-position of the estradiol or in the 3-position of the estradiol, an $NO_2$ group bonded to the oxygen atom.

These hormones may have the formula below:

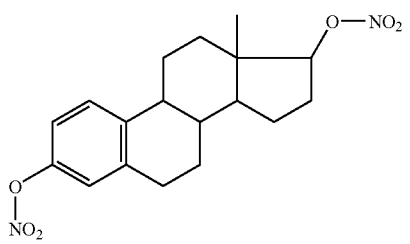

(V)

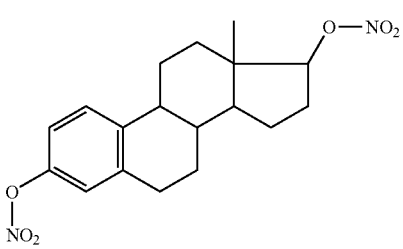

(VI)

In another embodiment of the invention, the hormone capable of binding to hormone receptors is spironolactone comprising an $NO_2$ group bonded to the hormone by means of a benzyloxy radical, preferably by means of a carboxylate group.

These hormones may have the formula below:

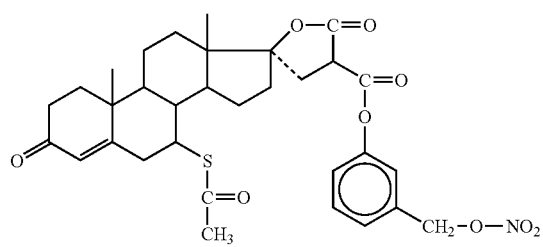

(VII)

It has been discovered that the compounds of the present invention defined above, including estradiol substituted in the 11- and/or 17-position with a nitric ester group, can be used in the prevention of premature births, in the control of uterine mobility and in increasing cervical dilatation during labor. These compounds can also be used in the treatment of uterine contraction anomalies and dysmenorrhea.

The compounds according to the invention are also advantageous in the context of replacement therapy for menopausal women, for inducing an artificial cycle in assisted reproduction and in the context of a use as an antihypertensive.

These properties justify their use in therapeutics, and a subject of the invention is particularly, as medicinal products, the compounds defined above in a pharmaceutically acceptable medium.

The compounds in accordance with the invention have, compared with unsubstituted steroid hormones, in particular the following advantages:
- a modification of their physicochemical properties, with easier and more even dissolution, better solubility,
- a more even pharmacological action, less variable over time and according to individuals,
- the obtaining of a selective accumulation and/or a delivery of nitrogen monoxide in tissues which have steroid receptors,
- an increase in activity due to the synergistic activity with the steroid molecule within the same tissue.

The various pharmaceutical forms and the routes of administration may be:
- for oromucosal use: oral or oromucosal tablets or such tablets in slow-release form, a gingival paste or gel, a lozenge to be chewed, a chewing gum, a pastille, an oromucosal capsule, drops, gel, a paste spray or any appropriate form of administration,
- for oral use: cachets, capsules, lozenges, coated lozenges, gastroresistant capsules or granules,
- for nasal use: a nasal spray, a solution for nasal inhalation, nasal drops or any other form of nasal administration,
- for vaginal use: an endocervical gel, an endocervical powder, a powder for an endocervical gel, a lozenge for use as a vaginal solution, a vaginal emulsion, a vaginal capsule, a vaginal cream, a vaginal foam, a vaginal gel, a vaginal irrigation, a vaginal solution or a vaginal suspension, a vaginal lozenge, a vaginal tampon or any other means which can be removed, for vaginal or cervical administration (such as an impregnated strip),
- for subcutaneous use: an intramuscular or subcutaneous administration (including a continuous infusion by means of a pump) or an intravenous administration such as a solution, suspension or emulsion,
- for topical or transdermal use: a patch, a cream, a powder or a spray.

The following examples illustrate the invention without, however, limiting it.

EXAMPLE 1

Preparation of the nitric ester of enol-3-pregna-3(4)5(6)-dien-20-one

Progesterone (one part of progesterone by weight) is dissolved in a mixture of 5 volumes of acetonitrile and of 2 volumes of tetrahydrofuran (THF) maintained at 0°. When the reaction is complete, a solution of para-toluenesulfonic acid in a proportion of 0.025 part in 0.25 volume of acetonitrile is added. A 65% solution of nitric acid (1.1 mol of nitric acid per mole progesterone) dissolved in 2 volumes of acetonitrile is then added. After a reaction time of approximately 30 minutes, the product is extracted with THF, and the solution is concentrated by evaporation and crystallized from isopropyl ether.

The progesterone enol nitrate of formula (I) is obtained.

EXAMPLE 2

Preparation of a Nitric Derivative of Progesterone of Formula (II)

Progesterone in a proportion of 1 part by weight is dissolved in a mixture of 5 volumes of acetonitrile and of 2 volumes THF maintained at 0°. When the reaction is complete, a solution of para-toluenesulfonic acid in a proportion of 0.025 part in 0.25 volume of acetonitrile is added. A solution of ethyl 4-nitroxymethylbenzoate (1.1 mol per mole of progesterone) dissolved in 2 volumes of acetonitrile is added. After a reaction time of approximately 30 minutes, the product is extracted with THF, and the solution is then concentrated by evaporation and crystallized from isopropyl ether.

EXAMPLE 3

Preparation of the Dinitric Ester of 17α-hydroxyprogesterone of Formula (III)

17α-Hydroxyprogesterone in a proportion of 1 part by weight is dissolved in 2.25 volumes of acetic anhydride (at least 98% pure) maintained at 0° C. A solution of 2.5% para-toluenesulfonic acid maintained at 0° C., in 0.25 volume of acetic anhydride, is then added. The mixture is carefully heated to a temperature of between 0 and 20°. A 65% solution of ethyl 4-nitroxymethyl-benzoate (1.1 mol per mole) in 2 volumes of acetonitrile is added. The mixture is maintained at 20° for one hour and then 0.05 part by weight of triethylamine is added and the product is mixed with 10 parts of a water+ice mixture. The product is filtered and washed and then redissolved in methanol which contains 10% of water, acidified with nitric acid (0.9 mol per mole) and refluxed for 2 hours. Three volumes of methylene chloride are then added. The product is neutralized, cooled, and extracted with methylene chloride. The methylene chloride is then eliminated and the product is crystallized from methanol.

EXAMPLE 4

Preparation of the 17α-hydroxypregn-4-ene-3,20-dione (4'-nitrooxymethyl)benzoate of formula (IV)

The esterification in the 17-position is carried out by increasing the nucleophilicity of the hydroxyl group by means of the formation of lithium alkoxide.

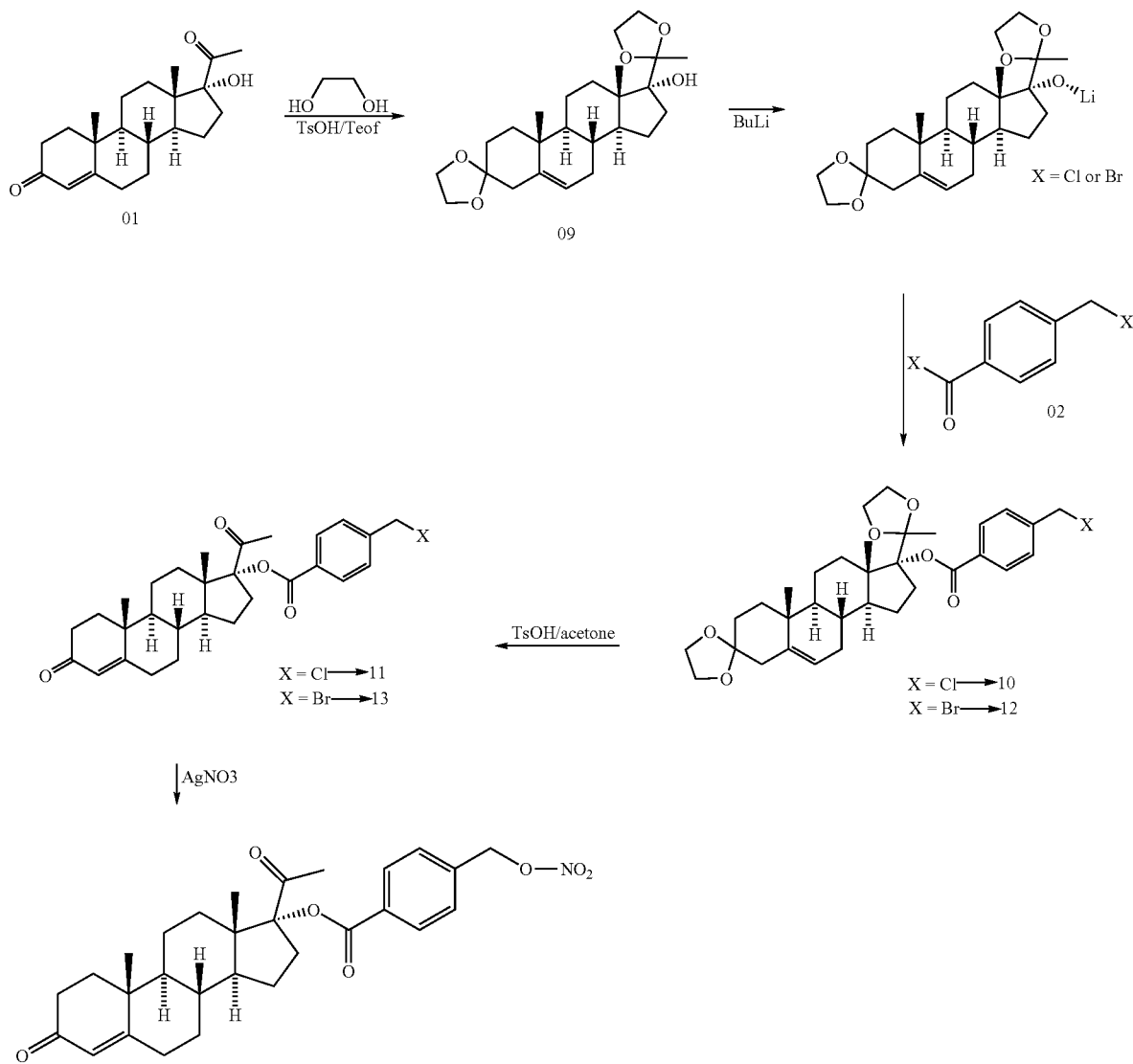

Under these conditions, after having obtained the ester 11 or 13, it was found to be relatively easy to continue to carry out the reaction with silver nitrate so as to obtain the compound described. In order to prevent side reactions during the formation of alkoxide, it is necessary to protect the carbonyl groups through the formation of the corresponding acetal.

Although 3 additional synthesis steps are necessary, all the reactions occur correctly and with good yields, it being possible to readily isolate and purify the intermediates.

The ketal 09 was readily obtained by reaction with ethylene glycol in the presence of TsOH (tosylic acid) as catalyst and triethyl orthoformate as dehydrating agent.

The product obtained is a white solid that can be readily purified by recrystallization from methanol.

Once purified, the product is treated in THF with BuLi (butyllithium) so as to form the alkoxide and it is left to react with the corresponding acid chloride (4-chloromethylbenzoic acid chloride or 4-bromomethyl-benzoyl bromide).

Unexpectedly, the reaction is finally carried out in 30 minutes, so as to give, quantitatively, the chloro ester 10 or the bromo ester 12 of the acetal.

The compounds 10 or 12 are readily hydrolyzed to a ketone in the presence of TsOH, so as to give the desired ester 11 or 13. These products are highly pure white solids. Not only can they be purified on a chromatographic column, but also by recrystallization from ethyl acetate.

All the intermediate products were characterized by NMR and the final product was characterized by NMR and mass spectrometry.

EXAMPLE 5

Preparation of the Nitric Ester of Estradiol of Formula (VI)

One part by weight of estradiol acetate is dissolved in 2 volumes of pyridine at 20° C., and nitrile chloride (in a proportion of 1.2 mol per mole) is added at 20° C. and maintained at this temperature for 4 hours. The product is then poured into a mixture of 10 parts of water and of ice and 2.5 volumes of hydrochloric acid, 22° Baumé, mixed at 0° C., washed and dried. The product is placed in methanol at reflux, 5 volumes, and crystallized from methanol. After drying, the estradiol bearing a nitric ester group in the 3-position is obtained with an 88% yield.

EXAMPLE 6

Preparation of a Dinitric Derivative of Estradiol of Formula (V)

One part by weight of estradiol is dissolved in a mixture of 5 volumes of acetonitrile and of 2 volumes of THF and maintained at 0°. A solution of 0.025 part of para-toluenesulfonic acid and 0.25 volume of acetonitrile is then added, followed by a 65% solution of nitric acid (2.5 mol per mole) in two volumes of acetonitrile, and the mixture is left to react overnight at 20° C. The product is extracted with methylene chloride and crystallized from isopropyl ether. Estradiol dinitrate is obtained.

EXAMPLE 7

Preparation of a Nitric Derivative of Spironolactone of Formula (VII)

0.116 part of metal sodium is added to 4 volumes of ethanol under a nitrogen atmosphere at 20° and refluxed until it is dissolved. The mixture is cooled to 30° and 1.288 parts of ethyl malonate are added, followed by the addition of one part of dienoxirane. The mixture is refluxed for 5 hours, cooled, and neutralized with 0.3 volume of acetic acid, and then 5 volumes of water are added. The precipitate is filtered, washed and dried. The carbaldiene is obtained with an estimated yield of 85%. A solution is prepared with one part of carbaldiene, 1.28 parts of 3-hydroxybenzyl nitrate, 0.75 part of dicyclohexylcarbodiimide and 20 volumes of dichloromethane. This solution is left at 20° overnight. The solvents are then concentrated, the dicyclohexylurea is eliminated by filtration and the product is crystallized from ethanol. The carboxydiene nitrate is obtained with an estimated yield of 80%.

The carboxydiene nitrate is then dissolved in 3.5 volumes of ethanol, and 0.4 part of thioacetic acid is added. The solution is refluxed for 3 hours and then cooled to 0° for one hour. The product is then dried. The spironolactone of formula (VII) is obtained with a yield of 94%.

EXAMPLE 8

Inhibition In Vitro of the Uterine Contractility of Myometreal Fibers from Uteruses of Women Who are Not Pregnant The contractile activity of human myometreal fragments was studied in vitro.

After a lag time of approximately two hours, allowing the establishment of spontaneous contractions, the inhibition of the contractions, produced by addition to the medium of 17α-hydroxyprogesterone and of its nitro derivative, 17α-hydroxypregn-4-ene-3,20-dione (4'-nitro-oxymethyl)benzoate, identified in this table under the name 17α-hydroxypregn-4-ene-3,20-dione (4'-nitro-oxymethyl)benzoate (example 4), could be measured.

This experiment makes it possible to evaluate the short-term effect of this compound.

The results are given in table I:

| | | PRODUCT | | | |
|---|---|---|---|---|---|
| | | 17α-hydroxypregn-4-ene-3,20-dione (4'-nitrooxy-methyl)benzoate | | 17α-hydroxy-progesterone | |
| | Concentration | Mean | Standard deviation | Mean | Standard deviation |
| Inhibition as % | $2 \times 10^{-7}$ M | 37 | 14 | 45 | 26 |
| | $2 \times 10^{-6}$ M | 69 | 6 | 66 | 29 |

The nitro derivative, 17α-hydroxypregn-4-ene-3,20-dione (4'-nitrooxymethyl)benzoate, has, on average, the same activity as hydroxyprogesterone, but its action is much more constant, less variable.

EXAMPLE 9

Inhibition In Vitro of Spontaneous or Induced Uterine Contractility in Uteruses from Non-Gestating Rats Intact 90-day-old female Old Wistar rats weighing 180 to 200 g are killed by decapitation the day after day II of the diestrous period. Their whole uncleaned uterus is removed and placed in a modified Kreb's Ringer solution (control buffer containing 2% of dimethyl sulfoxide) at 37°. The fat and the fascia covering the tissue are removed and the tissue is cut into small 5 mm rings. These rings are attached to a force displacement transducer under a tension of 1 gram. The tissue is left for a 30-minute equilibration period in order to allow the contractions to develop. The control buffer is replaced with a buffer which contains the test product (example 1 to 3) or progesterone alone in the presence or absence of the picrotoxin receptor antagonist. (32 µg/ml) or mifepristone (RU-486).

Various concentrations of the product tested are used to compare the uterus-relaxing effects of the test product with the effects of progesterone alone. No tissue ring is used in more than one control-test experiment. The tension for each type of experiment is measured over a period of 10 min. The uterine contractions are analyzed as total tension generated, in grams of tension per gram of tissue. The aim of this study is to show the uterus-relaxing activity of the product tested.

EXAMPLE 10

Inhibition In Vitro of Spontaneous and Induced Uterine Contractility in Uteruses from Gestating Guinea Pigs The aim is to measure the action of the test product on oxytocin-induced uterine contractions.

Mature guinea pigs at the 20th day of gestation are used. A 10 mm uterine segment is removed and suspended on a lever system (1 g) in an organ bath containing 35 ml of physiological solution (Van Dyke-Hasting) maintained at 37° and continually bubbled through with $O_2CO_2$.

The contractions are induced with oxytocin at a concentration of $10^{-4}$ mol/ml. The contractions are measured with a linear transducer coupled to a recording device. Addition of the test product at various concentrations shows the uterus-relaxing action whether the contractions of the uterus in gestation are spontaneous or induced. The action of these products is also compared to the action of progesterone.

EXAMPLE 11

Measurement In Situ of Contractility and of Arterial Pressure in Whole Uteruses

The uterine contractility is evaluated by measuring the changes in arterial pressure in a uterus perfused by means of a cannula in situ. Changes in arterial pressure are also determined. The measurement of the rate of uterine arterial blood flow in fact reflects the perfusion of this organ.

Five virgin female Hartley guinea pigs are anesthetized on day 1 of their estrus cycle (i.e. the first day of the opening of the vagina) with sodium pentobarbital at a concentration of 35 mg/kg. The external jugular vein is cannulated for administration of test product and the carotid artery is also cannulated in order to record arterial pressure. The uterus is exposed by means of medial abdominoperitoneal incision. A first cannula is inserted at the uterotubal junction and a second cannula is inserted, through the cervix, into the uterus and is fixed. The perfusion liquid (distilled water at ambient temperature) is perfused at a rate of 0.5 ml/min through the uterotubal junction cannula and is collected from the cannula present in the cervix. The product tested is administered and compared to progesterone. The modifications in the uterine perfusion pressure are recorded with Beckman pressure transducers coupled to a recording device. The responses in the uterine tone are quantified in terms of millimeters of mercury pressure. The modifications in arterial pressure are also recorded.

EXAMPLE 12

Measurement In Vivo of the Rate of Uterine Arterial Blood Flow and of the Systemic Pressure in Gestating Rats Gestating Wistar rats are anesthetized and mechanically ventilated with a ventilator for small rodents. The body temperature is maintained at 37°. The jugular vein is cannulated for the injection of test products and the systemic pressure is recorded from the left carotid artery. The uterus is then exposed and kept wet with a physiological solution. The principal uterine arterial rapidity is measured by means of a Doppler.

Administration of the product makes it possible to measure the influence of spontaneous or phenylephrine-induced uterine contractions and also to measure systemic pressure. This test can also be used in comparative studies with other products capable of relaxing the uterus, such as progesterone alone, NO donors or adrenergic antagonists, for instance ritodrine.

EXAMPLE 13

In Vivo Action of the Products According to the Invention on Labor in Gestating Rats The ability of the treatment with these drugs to delay the beginning of labor is evaluated in a model which measures the time for spontaneous delivery between the first and the second rat pup to be born in a full-term gestation.

Gestating females are placed in individual plastic cages from days 16 to 19 of gestation. From day 22, the females are continually observed. When the first rat pup is delivered, the females immediately receive the test product. The delivery time for the first rat pup is recorded and the female is then placed in its cage and observed until the second rat pup is delivered. The results are expressed as time-elapsed between the first and second deliveries.

The products administered are either the product which is the subject of the invention, or progesterone alone, or ritodrine or a placebo in order to compare the effects of these various products.

EXAMPLE 14

Action In Vivo on Uterine Cervical Maturation in Gestating Rats

The aim is to measure the cervical maturation of adult female rats. These gestating rats, at the end of the gestation period, exhibiting spontaneous or induced cervical maturation are treated with the test product, progesterone alone or the placebo, administered vaginally. The measurements of the amount of time to complete delivery, the force necessary to dilate the cervix and the amount of time to obtain dilatation are recorded.

EXAMPLE 15

Treatment of the Threat of Premature Delivery in Females a) By Injection:

A solution containing one of the compounds of examples 1 to 4 (derived from progesterone and from 17-hydroxyprogesterone) is reconstituted extemporaneously and infused subcutaneously by means of a catheter inserted under the skin and the use of a pump, at an initial dose of 1 mg to 10 mg per hour, according to the strength of the contractions. This dose can be increased very gradually if needed, under constant monitoring of arterial pressure. When a decrease in the frequency of the contractions is obtained, the dose can be very gradually decreased.

A solution containing one of the compounds of examples 1 to 4 (derived from progesterone and from 17-hydroxyprogesterone) is injected subcutaneously, by means of evenly spaced out injections. The use of methods normally used in galenics may make it possible to produce slow-release forms for controlled, slower and more prolonged diffusion of the active principle.

b) By Ingestion of a Tablet

A sublingual tablet containing one of the compounds of examples 1 to 4 is placed under the tongue without being swallowed or bitten. The initial dose is 3 mg. This can be taken two more times, with a one hour interval (9 mg in 2 hours in total), with continual monitoring of the arterial pressure. The dose intakes will then be repeated every 8 hours for a period of 48 hours.

c) By Means of an Intranasal Gel

An aqueous gel containing one of the compounds of examples 1 to 4, at a dose of 5 mg per unit dose, is applied in a nostril. This dose can be repeated three hours later, with continual monitoring of the arterial pressure. The applications are then repeated every 8 hours for a period of 48 hours.

d) By Means of an Intravaginal Gel

A gel containing one of the compounds of examples 1 to 4 is inserted into the vaginal cavity. The initial dose is 10 to 200 mg of active principle, with continual monitoring of the arterial pressure. A second administration will be carried out from 6 to 24 hours later.

The invention claimed is:

1. A compound wherein it has a formula selected from the group consisting of

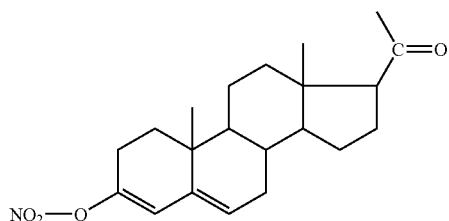

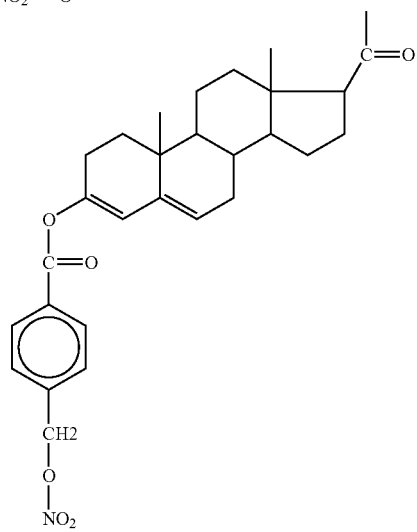

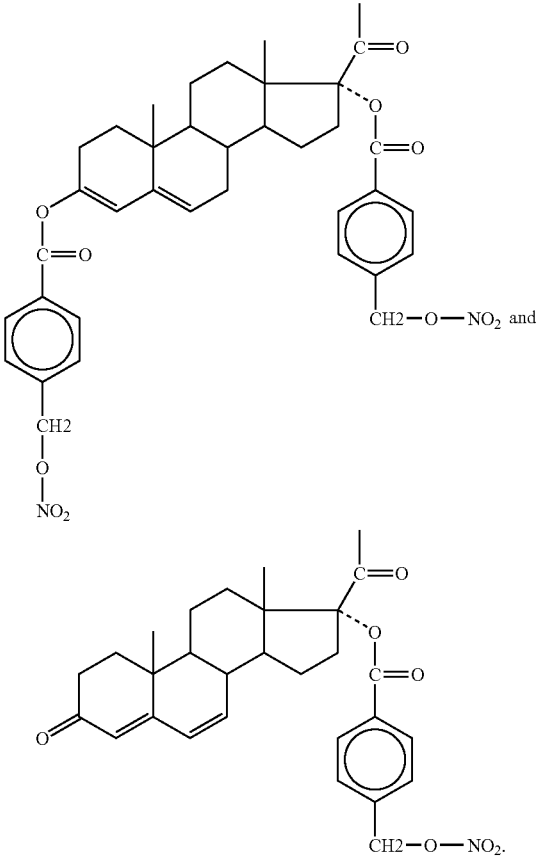

2. A method of controlling uterine mobility in women comprising administering to women in need thereof an amount of a compound of claim 1 sufficient to control uterine mobility.

3. A method of increasing cervical dilation during labor in women comprising administering to women in need thereof of an amount of a compound of claim 1 sufficient to increase cervical dilation.

4. A method of treating uterine contraction anomalies in women comprising administering to women in need thereof an amount of a compound of claim 1 sufficient to treat uterine contraction anomalies.

5. A method of treating dysmenorrhea in women comprising administering to women in need thereof an amount of a compound of claim 1 sufficient to treat dysmenorrhea.

6. A method of hormone replacement in menopausal women comprising administering to menopausal women in need thereof an amount of a compound of claim 1 sufficient for hormone replacement.

7. A method of treating arterial hypertension in women comprising administering to women in need thereof an amount of a compound of claim 1 sufficient to treat arterial hypertension.

8. A method of inducing an endometrial cycle in assisted reproduction in women comprising administering to women in need thereof an amount of a compound of claim 1 sufficient to induce an endometrial cycle.

* * * * *